United States Patent [19]

Klar

[11] 4,041,806
[45] Aug. 16, 1977

[54] TESTING CORD-TO-ELASTOMER ADHESION

[75] Inventor: Kenneth K. Klar, Cuyahoga Falls, Ohio

[73] Assignee: The Goodyear Tire & Rubber Company, Akron, Ohio

[21] Appl. No.: 733,583

[22] Filed: Oct. 18, 1976

[51] Int. Cl.$^2$ .................................... G01M 19/00
[52] U.S. Cl. .................... 73/159; 73/15.6; 73/146; 73/150 A; 73/96; 73/103
[58] Field of Search .......... 73/150 A, 146, 15.6, 73/67.3, 67.4, 160, 67.1, 141 R, 150 R, 141 A, 88 B, 96, 103, 159

[56] References Cited

U.S. PATENT DOCUMENTS

| 2,665,582 | 1/1954 | Armstrong | 73/159 |
| 3,470,732 | 10/1969 | Welhoelter | 73/15.6 |
| 3,550,427 | 12/1970 | Jungo Sueyoshi | 73/67.1 |

Primary Examiner—S. Clement Swisher
Assistant Examiner—Denis E. Corr
Attorney, Agent, or Firm—F. W. Brunner; R. S. Washburn

[57] ABSTRACT

The adhesion of cord or wire to the elastomer, rubber, or rubbery material is measured by exerting forces or loads collinear with the cords or wires such that one of the cords or wires is pulled from between a pair of cords. The three cords are embedded in a predetermined length of the elastomer. In a static test the opposing forces are exerted at a predetermined rate. In a dynamic test the opposing forces oscillate at predetermined frequency. Fixtures adapting an MTS high-speed oscillating tester are provided. The foregoing abstract is not to be taken as limiting the invention of this application, and in order to understand the full nature and extent of the technical disclosure of this application, reference must be made to the accompanying drawing and the following detailed description.

8 Claims, 4 Drawing Figures

TESTING CORD-TO-ELASTOMER ADHESION

The present invention relates to testing cord-to-rubber adhesion and particularly to a test for evaluating adhesion of cord or wire to rubber in tires.

Briefly summarized, the invention provides a method of testing a cord-to-rubber adhesion comprising selecting a specimen of cords embedded in a rubber matrix, said specimen having three parallel cords, applying force longitudinally of the first cord in a first direction and applying force to each cord of the pair thereof having the first cord therebetween in a second direction, and measuring the force required to cause separation between said first cord and said pair thereof.

For carrying out the method in accordance with the invention there is provided an apparatus for testing cord-to-rubber adhesion comprising means for exerting linear oscillation on a test specimen including a pair of rams arranged in opposing collinear alignment one being a fixed ram having a load cell and the other being a ram for effecting oscillation of a predetermined frequency and amplitude, a chamber disposed about said rams for controlling the test environment, a pair of fixtures each having a pair of clamp jaws and means for adjustably spacing said jaws relatively of one another, one of said fixtures being associated with the fixed ram the other of said fixtures being associated with the oscillating ram, one pair of said jaws being engageable to clamp opposite ends of a selected one of a plurality of parallel cords the other pair of jaws being engageable to clamp opposite ends of the pair of said cords having the selected cord there-between.

To acquaint persons skilled in the arts most closely related to the present invention certain preferred embodiments thereof illustrating the best mode now contemplated for putting the invention into practice are described herein by and with reference to the annexed drawings forming a part of this specification. The embodiments shown and described herein are illustrative and, as will become apparent to those skilled in these arts, can be modified in numerous ways within the spirit and scope of the invention defined in the claims hereof.

Figure 1:
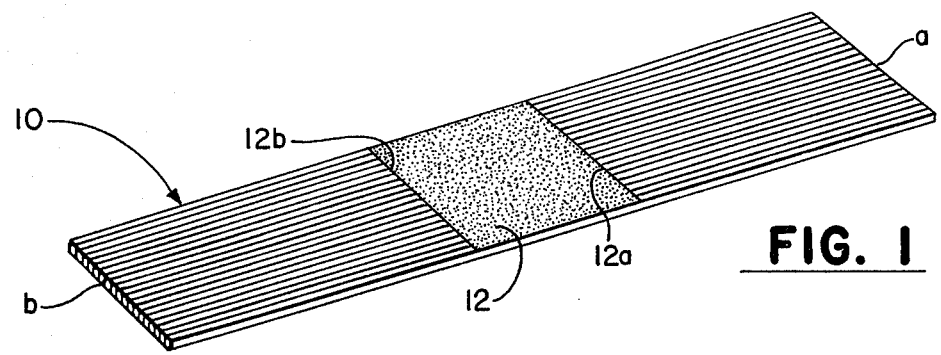
FIG. 1 is a schematic perspective illustration of a sample of cord ply stock according to the invention.

In FIG. 1 there is illustrated a sample or coupon 10 of cord ply stock. The sample comprises a plurality of parallel cords or wires extending in side-by-side array and embedded in a matrix of rubber compound. The sample would include a minimum of three parallel side-by-side cords.

The adhesive system which is the subject of the test is, normally, applied to the cords or wires after which the cords or wires are embedded in the matrix of rubber by a conventional calendering operation.

The sample, of suitable length in the direction of the cords or wires, and width measured transversely to the cords or wires and of a thickness equivalent to a single ply of the cord or wire ply stock. A length of about 6 inches (about 15 centimeters) has been found convenient. A width sufficient to provide a number of specimens 30 each of a minimum of three cords or wires is also convenient.

Figure 2:
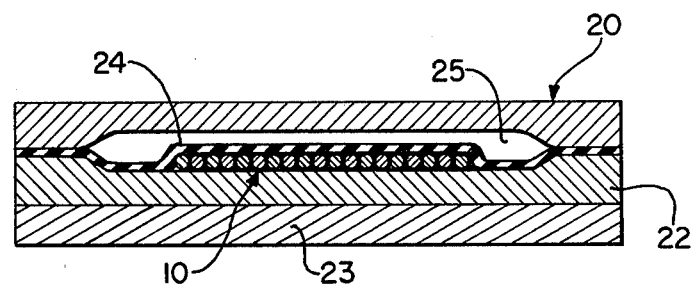
FIG. 2 is a schematic representation of a curing mold for use in preparing a specimen for testing according to the invention.

The sample or coupon can be cut from cord ply stock as received from the calender and the rubber suitably cured in a mold 20 between a heated plate 22 and an elastic diaphragm 24 which is urged against the plate by fluid pressure in the manner illustrated in FIG. 2.

The sample 10 may also be taken from a new tire by cutting the tire and separating therefrom a single ply for testing purposes. The sample may also be taken in the same manner from a tire which has been subjected to use in order that the effect of such use on the adhesive system may be determined.

The sample or coupon 10 may also be prepared by disposing a plurality of precut cords or wires in parallel array, embedding the cords or wires of the tests zone 12 of the sample in a suitable quantity of uncured gum rubber and then curing the specimen prior to testing in the manner illustrated in FIG. 2.

In the sample or coupon 10 a test zone 12 is marked off by lines 12a and 12b intermediate the respective ends a and b of the sample and the sample is then slit between each pair of cords outwardly from the lines 12a, 12b toward the respectively associated end of the sample. As illustrated in FIG. 1, the sample then comprises a test zone which is the intermediate portion of each test wire or cord embedded in undisturbed matrix of rubber, and end zones in which each of the cords or wires are individually separately accessible independently of one another.

Turning now to FIG. 2; uncured samples or coupons 10 may be cured in any convenient manner. It has been found convenient to dispose the sample on a plane rigid surface 23 provided with suitable heating means, for example, an electric resistance heater (not shown). An elastic diaphragm 24 is disposed over the sample 10. A fluid pressure chamber 25 is supplied with a fluid, e.g., compressed air, to urge the diaphragm toward the rigid surface with the sample 10 therebetween. The mold 20 can be placed in a conventional platen press for curing the sample. The mold described has the advantage of curing the test sample under conditions analogous to the curing of a tire having the cord ply stock therein.

A static cord-to-rubber test is conducted with a specimen 30 cut from the sample 10 of FIG. 1. To minimize edge effects, if any, one or more of the cords at the lateral edges of the sample are discarded. The specimen 30 of FIG. 3 may comprise three or five parallel cords which for convenience are identified A, B, C, D, E. As may be seen in FIG. 3, cords A, C and E are cut off or bent out of the way at the left of the test zone 12 and the cords B and D are extended from the test zone and held in the clamp 32. At the right of the test zone 12 cords B and D are cut off or bent out of the way while cords A, C and E are secured in clamp 34.

Clamps 32 and 34 are conventional and are provided in a tensile tester (not shown), for example, an Instron tensile tester well known to persons skilled in the arts. The clamp 32 is supported by a conventional load cell 36 and thence to the fixed bolster of the tensile test machine. The clamp 34 is attached to the movable bolster of the tensile test machine. The bolster and the clamp 34 are moved away from clamp 32 at a predetermined rate to apply tension to the specimen 30. As will be apparent, the cords or wires B and D extend in the test zone respectively between the pairs A,C and C,E. Thus, the tensile load is applied parallel to the direction of the cords and is resisted entirely by the adhesion of the respective cords to the surrounding matrix of rubber in the test zone 12 and the magnitude of the load applied and/or the elongation to the cords can be displayed and/or recorded by the tensile test machine to reveal the strength of the adhesion between the cords or wires and the surrounding rubber.

Test results can be obtained either as the maximum load applied or as the quantity of energy or work; i.e. the product of force and time, required to break the adhesive bond between the rubber and the cords or wires.

Figure 3:
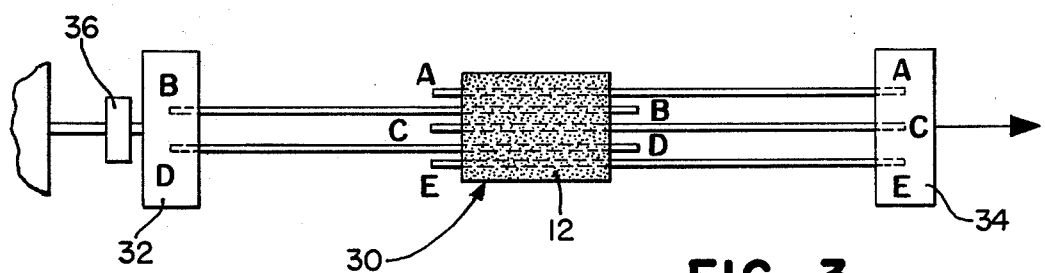
FIG. 3 is a schematic representation of a static test in accordance with the invention.
Figure 5:
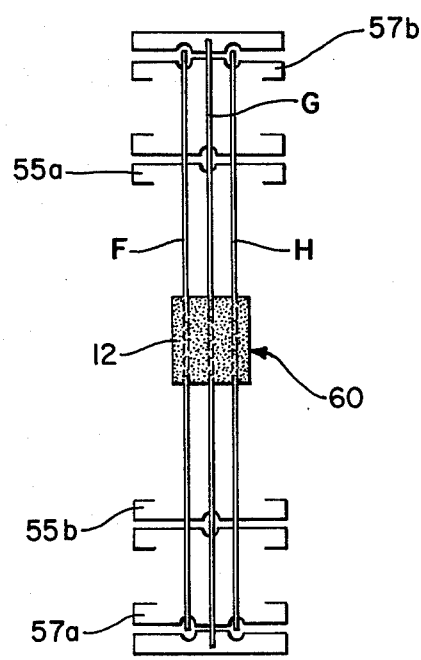
FIG. 5 is a schematic view of a test specimen in the apparatus of FIG. 4.

It will be apparent from an inspection of FIG. 3 that the static test described can be performed with a specimen from which the cords A and E have been omitted so that the specimen may consist of a group of three parallel cords only. In like manner, the number of cords in the specimen can readily be expanded to 7 or more parallel cords.

A dynamic adhesion test in accordance with the invention is performed by applying an initial tension to a first cord between a pair of clamps of a first fixture and applying an initial tension to each cord of a pair thereof having the first cord therebetween between a pair of clamps of a second fixture. One of the fixtures is then oscillated linearly relatively of the other, in a direction parallel to the cords or wires.

Figure 4:
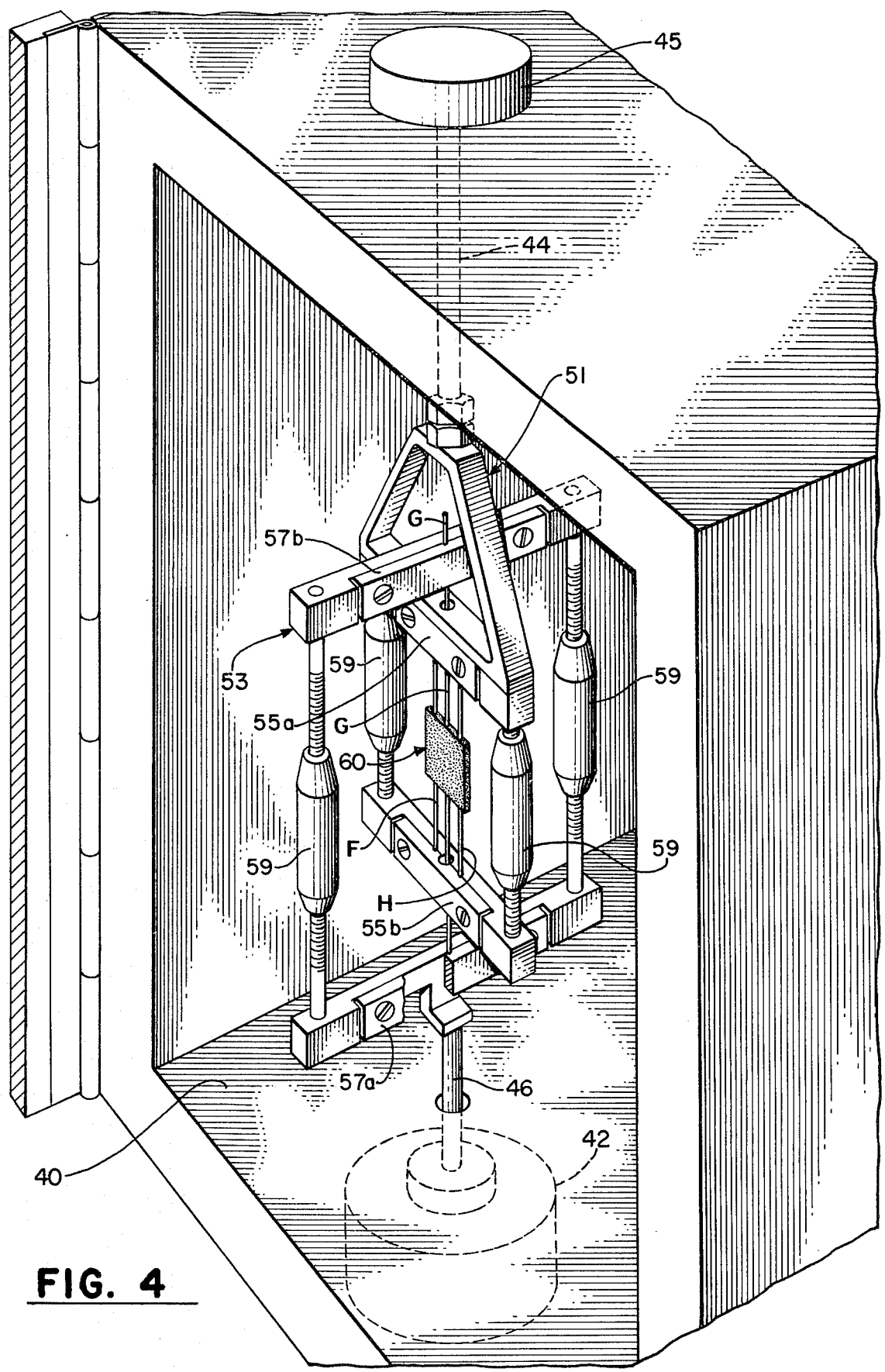
FIG. 4 is an illustration in perspective of an apparatus for performing a dynamic test in accordance with the invention.

The dynamic test is carried out, FIG. 4, in a chamber 40 providing a controlled environment in a tensile testing machine (not shown) having means 42 for exerting linear oscillation on a test specimen. In particular, an MTS high speed tester available from MTS Corporation of Minneapolis, Minn. has proved convenient for the purpose. This machine provides a fixed ram 44 having a load cell 45 from which applied load and its variations are communicated to a conventional display recorder (not shown), and an oscillating ram 46 connected to the oscillating means 42 capable of providing selected frequencies and amplitudes of oscillation to the ram 46. The respective rams are in collinear alignment and are adjustably spaced apart within the chamber 40.

Apparatus in accordance with the invention includes a first fixture 51 which is attached to the fixed ram 44 and a second fixture 53 which is attached to the oscillating ram 46. Each fixture provides a pair of clamps 55a, 55b and 57a, 57b, each pair being connected to each other by a parallel pair of turnbuckle devices 59 by which the respective clamps can be adjusted toward and away from each other to apply initial tension in the cords or wires of the test specimen 60. The respective clamps 55a, 57a each are provided with means for attachment to and removal from the respective test machine rams 44,46.

To carry out the dynamic adhesion test in accordance with the invention, a specimen 60 having a minimum of three cords or wires is taken from the sample 10 of FIG. 1. The center cord G of the three is secured at each of its respective ends in clamps 57a, 57b of the second fixture 53 attached to the oscillating ram 46. The parallel cords F,H on either side of the central cord are secured at their respective ends in the clamps 55a, 55b of the first fixture 51. The respective clamps of each fixture are then moved by the respecive turnbuckles 59 to apply a moderate initial tension in the wires or cords. The actual amount of tension is not significant and is applied only sufficiently to avoid buckling of the cord or lost motion between the clamps and the cords during the test.

With the environmental chamber 40 warmed to about 200° F. the oscillator drive means 42 applies an oscillation at a predetermined frequency and amplitude to the fixture 53 and particularly to the single cord G, oscillating it in the direction of its length, relative to the pair of cords, F,H held in the other fixture 51. An amplitude of about 0.020 inches at 60 cycles per second has been found suitable adequately to discriminate between specimens without requiring excessive testing time. Forces communicated from the oscillating ram through the specimen to the fixed ram and load cell 45 are displayed and/or recorded by the MTS tester.

The results of the dynamic adhesion test can be reported and compared as number of cycles to failure of the adhesion system and/or the integral product of load measured and time to failure of the specimen.

While certain representative embodiments and details have been shown for the purpose of illustrating the invention, it will be apparent to those skilled in the art that various changes and modifications may be made therein without departing from the spirit or scope of the invention.

What is claimed is:

1. A method of testing a cord-to-rubber adhesion comprising selecting a specimen of cords embedded in a rubber matrix, said specimen having three parallel cords, applying a force longitudinally of the first cord in a first direction and applying a force to each cord of the pair thereof having the first cord therebetween in a second direction, and measuring the force required to cause separation between said first cord and said pair thereof.

2. A method of testing a cord-to-rubber adhesion comprising providing a test specimen of cord ply having a matrix of rubber and a plurality of side-by-side parallel cords embedded therein, establishing a test zone of predetermined length parallel to said cords and extending transversely thereof intermediate the ends of the specimen, slitting said matrix between cords of each adjacent pair thereof outwardly from said zone to the respective ends of the specimen, gripping a first cord near one end of the specimen in a first clamp gripping each cord of the pair thereof having the first cord therebetween in a second clamp near the other end of the specimen, moving one of said clamps and the cord or cords gripped therein relatively of the other thereof in a direction parallel to said cords, and measuring the force exerted by said clamps to pull said first cord from between said pair thereof.

3. A method as claimed in claim 2, wherein providing said specimen includes inserting said specimen in an uncured state in a mold having a plane rigid surface and an elastic diaphragm, heating said surface while applying fluid pressure to urge said diaphragm toward said surface with the specimen therebetween to cure the specimen.

4. A method as claimed in claim 2, wherein said specimen is provided from cord or wire ply stock as delivered from a ply stock calender.

5. A method as claimed in claim 2, wherein said specimen is provided by cutting the same from a cured tire.

6. A method as claimed in claim 2, further comprising tensioning said first cord between said first clamp and an associated third clamp, tensioning each cord of said pair thereof between said second clamp and an associated fourth clamp, and oscillating said first and third clamp with said first cord held therein relatively of said second clamp and fourth clamp with said pair of cords held therein at a predetermined amplitude and frequency, and measuring the force and the time required to pull said first cord from between said pair of cords.

7. Apparatus for testing cord-to-rubber adhesion comprising means for exerting linear oscillation on a test specimen including a pair of rams arranged in opposing collinear alignment one being a fixed ram having a load cell and the other being a ram for effecting oscillation of a predetermined frequency and amplitude, a chamber disposed about said rams for controlling the test environment, a pair of fixtures each having a pair of clamp jaws and means for adjustably spacing said jaws relatively of one another, one of said fixtures being associated with the fixed ram the other of said fixtures being associated with the oscillating ram, one pair of said jaws being engageable to clamp opposite ends of a selected one of a plurality of parallel cords the other pair of jaws being engageable to clamp opposite ends of a pair of said cords having the selected cord therebetween.

8. Apparatus as claimed in claim 7, wherein said means for adjustably spacing said jaws comprises a parallel pair of turnbuckles extending between each respective pair of jaws parallel to the cord or cords clamped therein.

* * * * *